United States Patent [19]

Kirn

[11] Patent Number: 6,133,243

[45] Date of Patent: *Oct. 17, 2000

[54] LIPOSOMAL-VIRAL DNA COMPLEXES FOR TREATING DISEASE

[75] Inventor: David Kirn, Mill Valley, Calif.

[73] Assignee: Onyx Pharmaceuticals, Inc., Richmond, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/605,568

[22] Filed: Feb. 22, 1996

[51] Int. Cl.$^7$ .................................................. A61K 48/00
[52] U.S. Cl. ............................ 514/44; 435/375; 435/325
[58] Field of Search ............................ 514/44; 424/93.2, 424/320.1, 450; 935/52, 54; 435/375, 325

[56] References Cited

U.S. PATENT DOCUMENTS

| 4,925,661 | 5/1990 | Huang | 424/178.1 |
|---|---|---|---|
| 4,957,735 | 9/1990 | Huang | 424/178.1 |
| 5,043,164 | 8/1991 | Huang | 424/423 |
| 5,677,178 | 10/1997 | McCormick et al. | 435/325 |
| 5,801,029 | 9/1998 | McCormick et al. | 435/172.3 |
| 5,846,945 | 12/1998 | McCormick et al. | 514/44 |
| 5,856,181 | 1/1999 | McCormick et al. | 435/325 |

FOREIGN PATENT DOCUMENTS

| WO 94/18992 | 9/1994 | WIPO | A61K 35/76 |
|---|---|---|---|
| 95/12660 | 5/1995 | WIPO | |
| WO 95/12660 | 5/1995 | WIPO | |

OTHER PUBLICATIONS

Marshall, E (1995) Science 269:1050–1055.
Miller et al (1995) FASEB. J. 9:190–199.
Felgner, P., Advanced Drug Delivery Reviews, vol. 5:163–187, 1990.
J. Zabner et al., 'Cellular and Molecular Barriers to Gene Tranfer by a Cationic Lipid' Aug. 11, 1995 vol. 270 No. 32, pp 18997–19007 The American Society for Biochemistry and Molecular Biology, Inc.
W.–W. Zhang et al., 'Generation and Identification of Recombinant Adenovirus by Lipsome–Mediated Transfection and PCR Analysis' vol. 15, No. 5 pp. 868–872 BioTechniques.
N. Miller and Richard Vile, 'Targeted vectors for gene therapy' Feb. 1995 vol. 9 pp 190–199 The FASEB Journal.

*Primary Examiner*—Karen M. Hauda
*Attorney, Agent, or Firm*—Gregory Giotta

[57] ABSTRACT

Methods and compositions for treating cancer consisting of viral DNA in association with liposomal material, the viral DNA substantially incapable of encoding a functional viral oncoprotein capable of binding to a functional tumor suppressor gene product in a neoplastic cell, and the viral DNA capable of replicating and forming infectious virus in neoplastic cells thereby killing the neoplastic cells and substantially incapable of replicating and forming infectious virus in non-neoplastic cells that have the tumor suppressor protein.

10 Claims, No Drawings

LIPOSOMAL-VIRAL DNA COMPLEXES FOR TREATING DISEASE

FIELD OF THE INVENTION

This invention relates to treating disease, preferably after, using viral DNA that selectively replicates in, and lyse neoplastic but not normal cells. The invention will have significant applications for the treatment and diagnosis of cancer.

BACKGROUND OF THE INVENTION

It has been known for some time that a variety of cancers are caused, at least in part, by mutations to certain normal genes, termed "proto-oncogenes." Proto-oncogenes are involved in regulating normal cell growth in ways that are only now beginning to be appreciated at the molecular level. The mutated proto-oncogenes, or cancer causing genes termed "oncogenes," disrupt normal cell growth which ultimately causes the death of the organism, if the cancer is not detected and treated in time.

During normal or cancer cell growth, proto-oncogenes or oncogenes, are counterbalanced by growth-regulating proteins which regulate or try to regulate the growth of normal or cancer cells, respectively. Such proteins are termed "tumor suppressor proteins." A number of such proteins are known.

A gene that encodes a tumor suppressor protein termed p53 is frequently mutated in a number of human cancers, and the inactivation of p53 is thought to be responsible for the genesis or progression of certain cancers (Nigro et al., 1989, *Nature* 342:705–708), including human colorectal carcinoma (Baker et al., 1989, *Science* 244:217–221), human lung cancer (Takahashi et al., 1989, *Science* 246:491–494; Iggo et al., 1990, *Lancet* 335:675–679), chronic myelogenous leukemia (Kelman et al., 1989, *Proc. Natl. Acad. Sci. USA* 86:6783–6787) and osteogenic sarcomas (Madsuda et al., 1987, *Proc. Natl. Acad. Sci. USA* 84:7716–7719). Tumor cells that exhibit p53 are more sensitive to radiation treatment than tumor cells that have little or no p53.

Unfortunately, knowledge of the p53 status of tumors has not translated into new or more effective treatments for cancer. There are, however, reports showing that when p53 is supplied to a tumor cell that lacks p53, or expresses a non-functional mutated form of the molecule, certain types of breast and lung cancer cell lines exhibit normal cell growth, or undergo cell death. See Casey et al., Oncogene, vol. 6: 1791–1797 (1991), and Takahasi et al., Cancer Research, vol. 52: 2340–2342 (1992). These observations have stimulated efforts aimed at supplying to p53 minus cancer cells DNA that encodes wild type p53 via virus based gene transfer vehicles with the aim of causing the cancer cells to exhibit the normal cell phenotype, or undergo cell death. Unfortunately, the viral vectors that have been used to do these gene transfer experiments do not replicate in the host cancer cells that would effect the transfer of the p53 gene to neighboring cancer cells. Thus, for p53 gene therapy to be maximally successful every cancer cell in a patients' body must receive and express the DNA that encodes wild-type p53. To date this has not been achieved.

Another drawback relating to the delivery of tumor suppressors using viral vectors is the rejection of the vectors by a patient's immune system. Indeed, recent gene therapy trials with recombinant adenovirus carrying the gene that encodes the cystic fibrosis transmembrane conductance regulator protein were halted because of rejection of adenoviral proteins by the patients' immune system.

It has recently been described by McCormick (PCT/US94/02049, filed Feb. 16, 1994) that a recombinant adenovirus, dl1520, produced by Barker and Berk *Virology* vol.156: page 107–121 (1987), selectively replicates and lyse p53 minus cancer cells but not normal cells. Moreover, newly replicated virus was shown to be competent to infect and lyse neighboring cancer cells. Thus, in at least one respect, this finding is a marked advance over current gene therapy approaches which, to be maximally effective require that all cancer cells be infected following viral infection. This method, nevertheless, shares the drawback with the gene therapy approaches of immunologic rejection of the viral vector by the patient.

Thus, it is apparent that there is an unmet need for treating cancer, and particularly cancers that would respond favorably to treatment that takes advantage of the tumor suppressor status of a tumor, and that is not limited by a patient's immune system.

SUMMARY OF THE INVENTION

A first object of the invention is to describe methods and compositions for treating cancer consisting of administering to a patient an effective amount of a viral DNA complex by methods that reduce an immune response to intact virus, including encapuslation in a liposome, and direct injection into the cancer. The viral DNA is capable of producing infectious virions by selectively replicating and lysing neoplastic cells lacking certain tumor suppressor proteins, while not similarly affecting normal cells.

A second object of the invention is to describe methods and compositions for treating cancer consisting of administering to a patient an effective amount of adenoviral DNA by methods that reduce an immune response to intact virus including encapsulation in a liposome, and direct injection into the cancer. The adenoviral DNA preferably includes the E1A region of the viral genome, the E1B region less the region of E1B that encodes the viral oncoprotein, p55, and further includes other DNA sequences that enhance viral infection, lysis, or the production of progeny virus from the cancer cells.

A third object of the invention is to describe methods and compositions for treating cancer consisting of administering to a patient an effective amount of adenoviral DNA by methods that reduce an immune response to intact virus, including encapsulation in a liposome, and direct injection into the cancer. The adenoviral DNA preferably includes the E1A region of the viral genome, the E1B region less certain nucleotides that encode the viral oncoprotein p55 binding domain that interacts with and is responsible for binding of p55 to the tumor suppressor, p53, and further includes other DNA sequences that enhance viral infection and lysis, or the production of progeny virus from the cancer cells.

A fourth object of the invention is to describe methods and compositions for treating cancer consisting of administering to a patient an effective amount of adenoviral dl1520 DNA by methods that reduce an immune response to intact virus, including encasulation in a liposome and direct injection into the cancer.

A fifth object of the invention is to describe methods and compositions for treating cancer consisting of administering to a patient an effective amount of adenoviral dl1520 DNA by methods that reduce an immune response to intact virus, including encapsulation in a liposome consisting of cationic lipids and direct injection into the cancer.

A sixth object of the invention is a method for producing adenovirus that selectively replicates in, and lyse cancer cells but not normal cells.

These and other objects of the invention will become apparent upon a full consideration of the following disclosure.

DETAILED DESCRIPTION OF THE INVENTION

All the references described herein, including scientific publications, patents or patent applications, are intended to be fully incorporated by reference.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, the term "recombinant" indicates that a polynucleotide construct (e.g., and adenovirus genome) has been generated, in part, by intentional modification by man.

As used herein, the term "replication deficient virus" refers to a virus that preferentially inhibits cell proliferation or induces apoptosis in a predetermined cell population (e.g., cells substantially lacking p53 and/or RB function) which supports expression of a virus replication phenotype, and which is substantially unable to inhibit cell proliferation, induce apoptosis, or express a replication phenotype in cells comprising normal p53 and RB function levels characteristic of non-replicating, non-transformed cells. Typically, a replication deficient virus exhibits a substantial decrease in plaquing efficiency on cells comprising normal RB and/or p53 function.

As used herein, the term "p53 function" refers to the property of having an essentially normal level of a polypeptide encoded by the p53 gene (i.e., relative to non-neoplastic cells of the same histological type), wherein the p53 polypeptide is capable of binding an E1b p55 protein of wild-type adenovirus 2 or 5. For example, p53 function may be lost by production of an inactive (i.e., mutant) form of p53 or by a substantial decrease or total loss of expression of p53 polypeptide(s). Also, p53 function may be substantially absent in neoplastic cells which comprise p53 alleles encoding wild-type p53 protein; for example, a genetic alteration outside of the p53 locus, such as a mutation that results in aberrant subcellular processing or localization of p53 (e.g., a mutation resulting in localization of p53 predominantly in the cytoplasm rather than the nucleus) can result in a loss of p53 function.

As used herein, the term "RB function" refers to the property of having an essentially normal level of a polypeptide, herein termed p105, encoded by the RB gene (i.e., relative to non-neoplastic cells of the same histological type), wherein the RB polypeptide is capable of binding an E1a protein of wild-type adenovirus 2 or 5. For example, RB function may be lost by production of an inactive (i.e., mutant) form of RB or by a substantial decrease or total loss of expression of RB polypeptide(s). Also, RB function may be substantially absent in neoplastic cells that comprise RB alleles encoding a wild-type RB protein; for example, a genetic alteration outside of the RB locus, such as a mutation that results in aberrant subcellular processing or localization of RB, may result in a loss of RB function.

As used herein, the term "replication phenotype" refers to one or more of the following phenotypic characteristics of cells infected with a virus such as a replication deficient adenovirus: (1) substantial expression of late gene products, such as capsid proteins (e.g., adenoviral penton base polypeptide) or RNA transcripts initiated from viral late gene promoter(s), (2) replication of viral genomes or formation of replicative intermediates, (3) assembly of viral capsids or packaged virion particles, (4) appearance of cytopathic effect (CPE) in the infected cell, (5) completion of a viral lytic cycle, and (6) other phenotypic alterations which are typically contingent upon abrogation of p53 or RB function in non-neoplastic cells infected with a wild-type replication competent DNA virus encoding functional oncoprotein(s). A replication phenotype comprises at least one of the listed phenotypic characteristics, preferably more than one of the phenotypic characteristics.

The term "antineoplastic replication deficient virus" is used herein to refer to a recombinant virus which has the functional property of inhibiting development or progression of a neoplasm in a human, by preferential cell killing of infected neoplastic cells relative to infected non-replicating, non-neoplastic cells of the same histological cell type.

As used herein, "cancer", "neoplastic cells" and "neoplasia" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly-differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Frankly neoplastic cells are frequently referred to as cancer, typically termed carcinoma if originating from cells of endodermal or ectodermal histological origin, or sarcoma if originating from cell types derived from mesoderm.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, "physiological conditions" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl (or optionally KCl), pH6.5–8.1, and a temperature of approximately 20–45° C. Generally, physiological conditions are suitable binding conditions for intermolecular association of biological macromolecules. For example, physiological conditions of 150 mM NaCl, pH 7.4, at 37° C. are generally suitable.

Finally, it is important to note that while the instant invention is described in some detail in terms of its application to the treatment of cancer, it will be appreciated that it is more widely applicable to the treatment of diseases generally if a disease involves cells that lack functional tumor suppressor proteins, and the elimination or reduction of such cells benefits the patient.

Viral DNA

U.S. Pat. Ser. No. 08/198,184, filed Feb. 2, 1994, describes killing neoplastic cells by infecting the neoplastic cells with a recombinant adenovirus which is substantially replication deficient in non-neoplastic cells and which exhibits at least a partial replication phenotype in neoplastic cells. The difference in replication phenotype of the adenovirus constructs of the invention in neoplastic and non-neoplastic cells provides a biological basis for viral-based therapy of cancer. Expression of adenoviral cytopathic effects are correlated with the adenoviral replication phenotype characteristic of neoplastic cells infected with the recombinant adenovirus constructs, thus discriminating between neoplastic and non-neoplastic cells and providing selective cytotoxicity of neoplastic cells. The methods described are applicable to essentially any virus type wherein efficient replication requires binding and/or sequestration and/or inactivation of a host cell protein that is present in non-neoplastic cells but is substantially absent or nonfunctional in neoplastic cells (e.g., p53, RB). As mentioned above, this method represents a significant advancement in the field of cancer treatment. Nevertheless, administration of virus in this fashion suffers from the drawback of immunologic rejection.

Thus, the instant invention presents methods and compositions for treating cancer consisting of administering to a patient an effective amount of viral DNA delivered by methods that reduce an immune response to intact virus. One such method is by association with non or low immunogenic lipid, preferably in the form of a liposome. Another method is by particle mediated gene transfer. For the latter, viral DNA may be introduced into a patient's cells using the methods and apparatus described in U.S. Pat. Nos. 5,015,580 and 5,120,657. A preferred apparatus is Biolistics, PDS-1000/He System, Biorad Laboratories, Hercules, Calif. The appropriate viral DNA selectively replicates in, and lyse cancer cells lacking certain tumor suppressor proteins, such may include p53, to produce infectious virions, while not similarly affecting normal cells because such unaffected normal cells exhibit the tumor suppressor. The preferred viral DNA sequences are those that support viral replication and lysis in neoplastic but not normal cells. From such viral DNA may be deleted the DNA that encodes all or a part of the oncoprotein that binds a tumor suppressor. Consequently, the viral oncoprotein may be expressed, but would not be functionally capable of binding to and inactivating a tumor suppressor.

More preferred are viral DNA sequences that support viral replication and lysis in neoplastic, but not normal cells associated with the deletion of specific nucleotides from the gene that encodes a viral oncoprotein which effectively prevents the oncoprotein from binding to and inactivating the appropriate tumor suppressor. Numerous such oncoproteins are described by Hesketh, R., in The Oncogene Facts Book, Academic Press (1995). For example, the wild-type adenovirus E1b p55 oncoprotein binds to the cellular phosphoprotein p53. A function of p53 is to inhibit the progression of mammalian cells through the cell cycle. Thus, in infected cells that have p53 the oncoprotein p55 produces a substantial inactivation of p53 function. Functional E1b p55 protein is essential for efficient adenoviral replication in cells containing functional p53. Hence, adenovirus variants which substantially lack the ability to bind p53 are replication deficient in non-replicating, non-neoplastic cells having normal levels of functional p53.

Human tumor cells frequently are homozygous or heterozygous for mutated (e.g., substitution, deletion, frameshift mutants) p53 alleles, and lack p53 function necessary for normal control of the cell cycle (Hollstein et al. (1991) *Science* 253: 49; Levine et al. (1991) op.cit., incorporated herein by reference). Thus, many neoplastic cells are $p53^{(-)}$, either because they lack sufficient levels of p53 protein and/or because they express mutant forms of p53 which are incapable of substantial p53 function, and which may substantially diminish p53 function even when wild-type p53 may be present (e.g., by inhibiting formation of functional multimers). Some neoplastic cells may comprise alleles encoding essentially wild-type p53 proteins, but may comprise a second site mutation that substantially abrogates p53 function, such as a mutation that results in p53 protein being localized in the cytoplasm rather than in the nucleus; such second site mutants also substantially lack p53 function. It has been shown that replication deficient adenovirus species which lack the capacity to complex p53 but substantially retain other essential viral replicative functions exhibits a replication phenotype in cells which are deficient in p53 function (e.g., cells which are homozygous for substantially deleted p53 alleles, cells which comprise mutant p53 proteins which are essentially nonfunctional) but will not substantially exhibit a replicative phenotype in non-replicating, non-neoplastic cells. Such replication deficient adenovirus species are referred to herein for convenience as p53 minus, or E1b-$p53^{(-)}$ replication deficient adenoviruses.

As described in U. S. patent applications Ser. No. 08/198, 184 and PCT/US94/02049 now U.S. Pat. No. 5,677,178 a cell population (such as a mixed cell culture or a human cancer patient) which comprises a subpopulation of neoplastic cells lacking p53 function and a subpopulation of non-neoplastic cells which express essentially normal p53 function can be contacted under infective conditions (i.e., conditions suitable for adenoviral infection of the cell population, typically physiological conditions) with a composition comprising an infectious dosage of a E1b-$p53^{(-)}$ replication deficient adenovirus. This results in infection of the cell population with the E1b-$p53^{(-)}$ replication deficient adenovirus. The infection produces preferential expression of a replication phenotype in a significant fraction of the cells comprising the subpopulation of neoplastic cells lacking p53 function but does not produce a substantial expression of a replicative phenotype in the subpopulation of non-neoplastic cells having essentially normal p53 function. The expression of a replication phenotype in an infected $p53^{(-)}$ cell results in the death of the cell, such as by cytopathic effect (CPE), cell lysis, apoptosis, and the like, resulting in a selective ablation of neoplastic $p53^{(-)}$ cells from the cell population. Thus, with regard to adenovirus a considerable amount is known that enables a skilled practitioner of this art to select a particular virus, or construct mutants that exhibit altered p55 expression, and/or p55 binding to p53. The viral DNA may be isolated using techniques well known in the art, and administered to a patient as described herein. However, neither U.S. patent application Ser. No. 08/198,184 nor PCT/US94/02049 describe using adenoviral DNA with same properties of replication deficient adenovirus that replicates in and lyse p53$^{(-)}$ tumor cells by delivering the adenoviral DNA encapsulated in a liposome.

As mentioned above, typical viral oncoproteins include the adenoviral protein, p55, encoded by the E1b region of the virus, and the proteins encoded by the E6 and E7 regions of papillomavirus. p55 binds to the tumor suppressor p53, as mentioned above. The E6 and E7 regions of papillomavirus, and particularly of human papillomavirus strains HPV-16 and HPV-18, code for proteins of about 18kd and 20kd, respectively. The 18kd and 20kd proteins bind to p53 or Rb, respectively. Rb is a gene that encodes p105, a tumor suppressor protein present in normal retina cells. See, Hesketh, R., in The Oncogene Facts Book, page 324–330, Academic Press (1995).

Selectively killing tumor cells with liposome encapsulated viral DNA in lieu of the virus has the advantage of avoiding the immune response to intact virus. It is known that when adenovirus is administered to a patient the immune response to the virus is significant, and this has been, at least in part, responsible for the failure of those gene therapy trials that have sought to treat cystic fibrosis patients. A key feature of the present invention is that adenoviral DNA can be encapsulated in liposomal material. After administration, the viral DNA is taken up by both tumor and normal cells, and it will replicate in p53$^{(-)}$ tumor cells but not p53$^{(+)}$ normal cells. This will give rise to infectious viral particles and lysis of the tumor cells. The newly produced viral particles are capable of infecting other tumor and normal cells, and the immune response to these virions will depend on the site of the initial transfection with viral DNA. For example, if the site is the interior of a solid tumor, accomplished by direct inject of the viral DNA or other means, then the nascent infectious viral particles will escape early immune rejection since it is known that the interior of solid tumors is poorly accessible to the immune system.

The E6 and E7 regions of papillomavirus have been the subject of extensive mutational analysis for several years. Thus, a skilled practitioner of this art would know which virions to use and how to construct them to selectively kill cancer but not normal cells. Such virions are exemplified in a number of publications. See for example Crook, T., et al., Cell, vol. 67, pages 547–556 (1991), and Mietz, J. A., et al., EMBO J., vol. 11, pp. 5013–5020 (1992). Thus a skilled practitioner could construct papillomavirus with E6 or E7 deleted, or mutated such that when the DNA is incorporated into a liposome and transfected into the appropriate cancer cell it will preferentially lyse p53$^{(-)}$ or p105$^{(-)}$ tumor cells, respectively. It is important to note that the antineoplastic effect of papillomaviral DNA may be preferred for use with cancer cells of epithelia origin since this is the apparent cell type specificity of the virus.

Thus, it will be apparent that using viral DNA liposomal constructs as described herein, and by selectively administering the constructs directly into certain types of tumors that the immune rejection of the liposomal DNA constructs, and subsequently produced viral particles is minimized.

Typically, viral DNA will be isolated from E1b-p53$^{(-)}$ replication deficient adenovirus constructs suitable for selective killing of p53$^{(-)}$ neoplastic cells and will consist of mutations (e.g., deletions, substitutions, frameshifts) which inactivate the ability of the E1b p55 polypeptide to bind p53 protein effectively. Such inactivating mutations typically occur in the regions of p55 which bind p53.

Viral DNA may be isolated from a number of virions, including suitable E1b-p53$^{(-)}$ replication deficient adenovirus constructs for use in the methods and compositions of the invention. Such would include, but are not limited to the following examples: (1) adenovirus type 2 dl 1520, which contains a C to T mutation at nucleotide position 2022 that generates a stop codon 3 amino acids downstream of the AUG codon used for initiation of translation of the p55 protein and a deletion between nucleotides 2496 and 3323 replaced with a small linker insertion that generates a second stop codon at nucleotide 3336; the expression of the p19 protein is essentially unaffected (Barker and Berk (1987) Virology 156: 107, incorporated herein by reference, and (2) a composite adenovirus construct comprising adenovirus type 2 dl 1520 comprising at least the position 2022 mutation and/or the 2496–3323 deletion mutation, or a substantial portion thereof, and an additional mutation in p19 to yield a p19 cyt mutant; the composite virus construct lacks p55 and comprises the enhanced cytopathic effect of the p19 cyt mutation. Ad2 dl 1520 are available from Dr. A. Berk, University of California at Los Angeles, Los Angeles, Calif., and are described in the literature, including Barker and Berk (1987) Virology 156: 107, incorporated herein by reference.

It is desirable for the mutant virus from which viral DNA is isolated to be replicable and to form infectious virions containing the mutant viral genome which will spread and infect other cells, thus amplifying the antineoplastic action of an initial dosage of liposome encapsulated viral DNA. Adenoviral DNA can be isolated from additional E1b$^{(-)}$ mutants lacking the capacity to bind p53 by those of skill in the art by generating mutations in the E1b gene region encoding the p55 polypeptide, expressing mutant p55 polypeptides, contacting the mutant p55 polypeptides with p53 or a binding fragment of p53 under aqueous binding conditions, and identifying mutant E1b polypeptides which do not specifically bind p53 as being candidate E1b$^{(-)}$ mutants suitable for use in the invention.

More typically, a functional assay will be used to identify candidate E1b$^{(-)}$ mutants from which viral DNA will be isolated. For example, the Friend assay for determination of p53 function will be performed essentially as described in Frebourg et al. (1992) Cancer Res. 52: 6977, incorporated herein by reference. E1b mutants which lack the capacity to inactivate p53 will be identified as candidate E1b$^{(-)}$ replication deficient mutants.

The materials and methods for isolating adenovirus, and viral DNA are well known in the art. See for example, Hitt, M., Bett, A. J., Prevec, L. and Graham, F. L. Construction and propagation of human adenovirus vectors. In: Cell Biology: a Laboratory Handbook; J. Celis (Ed), Academic Press, N.Y. in press; Graham, F. L. and Prevec, L. Manipulation of adenovirus vectors. In: Methods in Molecular Biology, Vol. 7: Gene Transfer and Expression.

Lipsomal Encapsulation

Liposome transfection of viral DNA can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3β[N-(N N-dimethylaminoethane)-carbarmoyl cholesterol (DC-Chol), as well as other lipids known to those of skill in the art. Catatonic liposomes as described by Gao et al., Biochemical and Biophysical Research Communications, vol. 179: pages 280–285. (1991) are preferred in the instant invention. Gao et al describes a novel catatonic cholesterol derivative that can be synthesized in a single step. Liposomes made of this lipid are more efficient in transfection and less toxic to treated cells than those made with the reagent Lipofectin™.

Those of skill in the art will recognize that there are a variety of liposomal transfection techniques which will be useful in the present invention. Among these techniques are those described by Nicolau et al., Methods in Enzymology, vol. 149: pages 157–176 (1987) and Liposomes comprised of DOTMA, such as those which are available commercially under the trademark Lipofectin™, from Vical, Inc. (San Diego, Calif.) may also be used.

Liposomes may be introduced into contact with cells to be transfected by a variety of methods. In cell culture, the liposomes are simply dispersed in the cell culture solution. However, for application in vivo liposomes are typically injected. The preferred method, as mentioned above, is direct injection into the tumor to limit immune rejection of the viral DNA. However, other modes of administration may be used. Intravenous injection allows liposome-mediated transfer of the viral DNA to target the liver and the spleen.

The lipid employed to make the liposomal complex can be any of the above-discussed lipids. In particular, DOTMA, DOPE, and/or DC-Chol may form all or part of the liposomal complex. In a preferred embodiment, the lipid will comprise DC-Chol and DOPE consisting of a ratio of DC-Chol:DOPE between 1:20 and 20:1. More preferred are liposomes prepared from a ratio of DC-Chol:DOPE of about 1:10 to about 1:5.

As mentioned above, intravenously injected liposomes are taken up essentially in the liver and the spleen by the macrophages of the reticulendothelial system. The specific site of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, Biol. Cell, vol. 47: pages 121–130 (1983). Thus, liposomal viral DNA Complexes of the inventions can effectively be targeted to tumors of the liver and/or spleen that originate in these regions, or to tumors that originate elsewhere and metastasize to these organs.

Intravenous injection is one means of realizing site specific delivery of the liposome encapsulated viral DNA sequences. Such can be delivered selectively to the appropriate target tumor cells by other means, and a preferred means is via a catheter, as described by Nabel et al., Science, vol. 249: pages 1285–1288 (1990). For example, Nabel et al., above, teach injection via a catheter into the arterial wall. Importantly, these methods permit delivering of the liposome viral DNA sequences at a specific site in vivo, and not just to the liver and spleen cells which are accessible via intravenous injection.

Formulation and Uses

Certain methods of preparing dosage forms of the invention lipsomal viral DNA compositions are known. See, e.g., Remington's Pharmaceutical Sciences, Mack Publishing Company, Easton, Pa., 17th edition, 1985. The composition or formulation administered will contain a predetermined quantity of the viral DNA to achieve the desired anti-tumor effect.

The various compositions of the present invention will preferably be used in combination with pharmaceutically acceptable excipient materials. Preferred pharmacologically acceptable excipients include neutral saline solutions buffered with phosphate, lactate, Tris, and other appropriate buffers known in the art.

The liposomal viral DNA complexes of the invention may be used to detect the presence of cells lacking certain tumor suppressor proteins including p53 and/or p105 function. For example, a cell sample comprising a subpopulation of neoplastic cells lacking p53 and/or p105 can be transfected with a suitable adenovirus or papillomavirus liposomal complex as discussed above. After a suitable incubation period, the cells in the cell sample that express a replication phenotype (e.g., loss of ability to exclude Trypan blue, virion formation, $^3$H-thymidine incorporation into viral DNA) can be quantified to provide a measure of the number or proportion of replicative and/or neoplastic cells in the cell sample. Such methods may be used to diagnose neoplasms and/or evaluate tumor cell load.

Alternative diagnostic uses are apparent; for example, a reporter gene [e.g., luciferase, b-galactosidase, Green Flurosent Protein (See WO 95 07463)] may be substituted for a negative selection gene in a replication deficient adenovirus; transformed cells may be scored (such as in a cellular sample or transformation assay) by the expression of the reporter gene, which is correlated with expression of a replication phenotype indicating a lack or presence of p53 and/or p105 in a cell.

Therapy of certain neoplastic diseases may be afforded by administering to a patient a composition comprising the liposomal viral DNA complexes discussed above. Preferred are complexes containing viral DNA from replication deficient adenoviruses E1b-p53$^{(-)}$, or papillomavirus constructs with E6 or E7 deleted or mutated as discussed above. Such adenovirus or papillomavirus liposomal complexes may include, as part of the viral DNA a selectable marker, and preferably a negative selection gene.

Various human neoplasms comprising cells that lack p53 and/or RB functions may be treated with the appropriate liposomal viral DNA complexes. For example, a human patient or nonhuman mammal having a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukemia may be treated by administering an effective antineoplastic dosage of an appropriate adenovirus E1b-p53$^{(-)}$ liposomal complex. Viral DNA liposomal suspensions may be applied to neoplastic tissue by various routes, including intravenous, intraperitoneal, intramuscular, subdermal, and topical. A viral DNA liposomal suspension may be inhaled as a mist (e.g., for pulmonary delivery to treat bronchogenic carcinoma, small-cell lung carcinoma, non-small cell lung carcinoma, lung adenocarcinoma, or laryngeal cancer) or swabbed directly on a tumor site (e.g., bronchogenic carcinoma, nasopharyngeal carcinoma, laryngeal carcinoma, cervical carcinoma) or may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g., a breast tumor), enema (e.g., colon cancer), or catheter (e.g., bladder cancer). The advantages of the latter method have already been discussed.

Viral DNA liposomal complexes may be formulated for therapeutic and diagnostic administration to a patient having a neoplastic disease. For therapeutic or prophylactic uses, a sterile composition containing a pharmacologically effective dosage of one or more species of antineoplastic replication deficient adenovirus mutant DNA is administered to a human patient or veterinary non-human patient for treatment of a neoplastic condition. Generally, about 0.5–50 ug of viral DNA with liposome will be administered per treatment in an aqueous suspension. A pharmaceutically acceptable carrier or excipient is often employed in such sterile compositions.

A variety of aqueous solutions can be used, e.g., water, buffered water, 0.4% saline, 0.3% glycine and the like. These solutions are sterile and generally free of particulate matter other than the desired viral DNA liposomal complex. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance transfection of cells by the complexes may be included.

The viral DNA liposomal complexes may be delivered to neoplastic cells on the basis of a cell surface property present on the neoplastic cell population. For example, the presence of a cell surface protein associated with neoplastic cells which binds an immunoglobulin can be exploited by attaching the immunoglobulin to the exterior surface of the liposome to target the liposome containing viral DNA to the neoplastic cell. Such liposomes are termed "immunoliposomes." Typically, an aqueous suspension containing viral DNA is encapsulated in immunoliposomes. For example, a suspension of replication deficient adenovirus DNA can be encapsulated in liposomes to form immunoliposomes by conventional methods (See, for example, U.S. Pat. No. 5,043,164, U.S. Pat. No. 4,957,735; U.S. Pat. No. 4,925,661; Connor and Huang (1985) *J. Cell Biol.* 101: 582; Lasic DD (1992) *Nature* 355: 279; *Novel Drug Delivery*(eds. Prescott LF and Nimmo WS: Wiley, New York, 1989); and Reddy et al. (1992) *J. Immunol.* 148: 1585.)

Immunoliposomes comprising an antibody that binds specifically to a cancer cell antigen (e.g., CALLA, CEA) present on the cancer cells of the individual may be used to target viral DNA to those cells.

The viral liposomal complexes described herein can be administered for prophylactic and/or therapeutic treatments of neoplastic disease. For therapeutic applications, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

In prophylactic applications, compositions containing the antineoplastic replication deficient adenoviral DNA, or cocktails thereof are administered to a patient not presently in a neoplastic disease state to enhance the patient's resistance to recurrence of a neoplasm or to prolong remission time. Such an amount is defined to be a "prophylactically effective dose." In this use, the precise amounts again depend upon the patient's state of health and general level of immunity.

Single or multiple administrations of the compositions can be carried out with dose levels selected by the treating physician. In any event, the pharmaceutical formulations should provide a quantity of the antineoplastic viral liposome complex of this invention sufficient to effectively treat the patient. Antineoplastic viral liposomal therapy of the present invention may be combined with other antineoplastic protocols, such as conventional chemotherapy.

The invention is demonstrated by the following examples. However, while these examples are exemplary of the invention, it will be appreciated by those of skill in the art that certain modifications and alterations may be made without departing from the spirit and scope of the invention.

EXAMPLE 1

Preparation of Liposome/Viral DNA Complexes

Catatonic liposomes are used to effect efficient transfection of the appropriate viral DNA into neoplastic cells. Such catatonic liposomes can be prepared using the method of Gao et al., Biochemica and Biophysical Research Communications, vol. 179: pages 280–285 (1991), and are a mixture of DC-Chol ("3B(N-(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 umol of DC-Chol and 8.0 umol of DOPE in chloroform. This mixture is then dried, vacuum desiccated, and resuspended in 1 ml sterol 20 mM HEPES buffer (pH 7.8) in a tube. After 24 hours of hydration at 4° C., the dispersion is sonicated for 5–10 minutes in a sonicator to form liposomes with an average diameter of 150–200 nm. To prepare a liposome/DNA complex, the following steps are followed. Firstly, viral DNA is isolated and purified from the E1B$^{(-)}$ adenovirus mutant, dl1520, as described by Barker and Berk *Virology* vol.156: page 107–121 (1987). The materials and methods for isolating adenovirus, and viral DNA are well known in the art. See, for example, Hitt, M., Bett, A. J., Prevec, L. and Graham, F. L., Construction and propagation of human adenovirus vectors, In: Cell Biology: a Laboratory Handbook; J. Celis (Ed), Academic Press, N.Y. In press; Graham, F. L. and Prevec, L. Manipulation of adenovirus vectors, In: Methods in Molecular Biology, Vol. 7: Gene Transfer and Expression.

Dl1520, is grown on the human embryonic kidney cell line HEK293, and the cells infected with the virus at a MOI of 1–10 and incubated until cytopathic effect is visible. The 293 cell line is available from the American Type Culture Collection, #CRL 1573, Rockville, Md.; See also, Graham et al. (1977) *J. Gen. Virol.* 36: 59. The cells are harvested and pelleted by low speed centrifugation. Virus is extracted from the cell pellet by three consecutive freeze/thaw cycles and collected in the supernatant by centrifugation at 10,000×g for 30 minutes. This crude cell lysate is purified by ultracentrifugation over a series of two CsCl gradients, followed by dialysis against a 500-fold volume of buffer. Aliquots of the purified virus are stored at −70° C. The titer of purified virus is determined by a plaque assay in which HEK293 cells are infected with serially diluted virus, overlaid with growth media containing agarose, and incubated until quantifiable plaques appear on the monolayers. Next, viral plasmid DNA is isolated and purified using methods well known in the art, as referred to above.

The adenoviral dl1520 DNA is placed in DMEM/F12 medium in a ratio of 15 $\mu$g DNA to 50 $\mu$l DMEM/F12. DMEM/F12 is then used to dilute the DC-Chol/DOPE liposome mixture to a ratio of 50 ul DMEM/F12 to 100 ul liposome. The DNA dilution and the liposome dilution are then gently mixed, and incubated at 37° C. for 10 minutes. Following incubation, the viral DNA/liposome complex is ready for use.

EXAMPLE 2

Regression of Solid Tumors With AdenoViral DNA Liposomal Complexes

Experiments are conducted to show that certain adenoviral DNA complexes are effective to eliminate or reduce the growth of solid tumors, preferably when administered internally to the tumor to limit immune rejection. The cell line C33A is chosen to carry out the experiment. C33A is a human cervical carcinoma cell line; it is available from the American Type Culture Collection, Rockville Md. The cell line is chosen primarily for two reasons: firstly, it substantially lacks the tumor suppressor protein, p53, and secondly, it grows as a solid tumor. The latter property affords the opportunity to demonstrate the concept that adenoviral DNA can be delivered in a liposome and to the relatively immune inaccessible site, the central region of a C33A solid tumor.

The liposomal adenoviral DNA complexes are prepared as described in Example 1 from the adenovirus mutant dl1520. See, Barker and Berk *Virology* vol.156: page 107–121 (1987). This DNA is effective for treating tumors that lack the tumor suppressor protein p53.

The experiment is conducted as follows. Female athymic nu/nu nude mice (7–10 weeks old) in groups of 5 are given subcutaneous injections into both flanks with $5 \times 10^6$ C33A cells in 0.2 ml of phosphate buffered saline. The cells are grown under standard cell culture conditions in Dulbecco's Modified Eagles Medium supplemented with Fetal Bovine Serum, amino acids and antibiotics, and passaged at confluency with trypsin.

The tumors are allowed to grow until they are between 0.15 and 0.40 ml in volume, which generally will take about 1 month. Tumor volume is calculated by multiplying the largest tumor diameter (length) and its perpendicular (width) squared, divided by 2: (length/width$^2$). At the end of the 1 month period mice are divided into 4 groups.

Mice in group 1 are injected with viral DNA alone, group 2 injected with liposomal viral DNA complex prepared in the manner described above, group 3 injected with a liposomal viral DNA complex containing DNA isolated, also as described above, from the replication defective adenovirus Ad-alpha1 AT. This virus contains the DNA that encodes alpha1-antitrypsin, and is on deposit with the American Type Culture Collection with accession number CCL 248. This virus is deleted in the E1A and E1B regions of the viral genome.

Finally, as a further control, mice in group 4 are injected with liposome alone. Mice are injected every other day over the course of the experiment which lasts for 6 weeks. At its conclusion, tumor measurements are taken, and the mice observed for overall appearance and activity. Mice surviving at the end of the experiment are sacrificed and necropsied. Tumors are excised, weighed, measured, and examined histologically for tumor necrosis and infiltration of the tumor by immune effector cells.

An analysis of the data at the end of the 6 week period would reveal that mice in group 2 would display statistically significantly lower mean tumor weights compared to mice in groups 1, 3, and 4.

To confirm that the reduction in tumor weights is due to adenovirus production resulting from adenoviral DNA liposomal mediated transfection, tumor tissue from group 2 mice is prepared for immunohistochemical staining to detect adenovirus hexon protein. The procedure, well known in the art, would employ antibody to adenovirus type 2 hexon protein and immunoperoxidase. The tumor tissue, but not surrounding normal tissue, would stain positively for hexon protein.

Taken together these data establish that adenoviral DNA isolated from the viral mutant dl1520 and encapsulated in a liposome can be transfected into p53$^{(-)}$ tumor cells to produce infectious virus that lyse the tumor cells, and thus are beneficial for the treatment of cancer.

EXAMPLE 3

Prevention of Ovarian Tumors in Nude Mice With AdenoViral DNA Liposomal Complexes The liposomal adenoviral DNA complexes are prepared as described in Example 1 from the adenovirus mutant dl1520. See, Barker and Berk *Virology* vol.156: page 107–121 (1987). As mentioned previously, this DNA is effective for treating tumors that lack the tumor suppressor protein p53, and its antineoplastic effect can be demonstrated against ovarian p53$^{(-)}$ tumor cells as follows.

Female nude mice (5–6 weeks old) in groups of 5 are given intraperitoneal injections of SK-OV-3 cells ($2 \times 10^6$/100 µl). SK-OV-3 cells are human ovarian cancer cells that are p53$^{(-)}$, and that have been shown to grow within the peritoneal cavity of nude mice. The neoplastic cell lines tested may be obtained from the American Type Culture Collection, Rockville, Md. After five days the mice are given intraperitoneal injections as follows. Mice in group 1 are injected with dl1150 viral DNA alone, group 2 injected with liposomal dl1150 viral DNA complex prepared in the manner described above, group 3 injected with a liposomal viral DNA complex, also purified as described above, containing DNA isolated from the replication defective adenovirus Ad-alpha1 AT, described above.

Finally, as a further control, mice in group 4 are injected with liposome alone. Mice are injected every other day over the course of the experiment which lasts for about 9 months. 200 µl of a given sample is injected intraperitoneally into a given mouse. After the initial injections, injections are repeated every seven days throughout the course of the experiment.

The results would reveal that mice in groups 1, 3 and 4 develop extensive ascites, and would die on average about 2 months after the injection of the SK-OV-3 cells. In contrast mice in group 2 would still be alive at the completion of the experiment, or after 9 months.

These results would establish that liposome-mediated gene transfer of the adenoviral genome lacking a funtional gene that encodes the protein, p55, that binds to the tumor suppressor p53 is an effective antineoplastic agent against human ovarian cancer cells.

These experiments would further show that administration of replication-deficient recombinant adenovirus DNA as part of a liposomal complex can be used to selectively kill neoplastic cells, and that this effect is not restricted to a particular tumor cell type.

What are believed to be the preferred embodiments of the invention have been set forth above, nevertheless it will be appreciated by the skilled practitioner of this art that there are other changes and modifications that may be made to the invention without departing from the spirit of the invention and that it is the intent of the inventors to claim all such changes and modifications.

I claim:

1. A method for treating cancer in a mammal in need of said treatment, said cancer comprising a cell population of non-neoplastic and neoplastic cells, comprising the steps of;

administering to said animal at the site of said tumor an effective amount of a complex consisting of liposomal viral DNA, said viral DNA being substantially purified adenoviral DNA not in an expression vector and that lacks an expressed viral oncoprotein capable of binding to a functional p53 tumor suppressor protein, and said viral DNA having the further properties of replicating and forming infectious virus in said neoplastic cells that lack functional p53 thereby killing said neoplastic cells and substantially incapable of replicating and forming infectious virus in non-neoplastic cells that have said p53 tumor suppressor protein.

2. A method for treating cancer in an animal as described in claim 1 wherein said adenoviral DNA includes the E1A and E1B regions of the viral genome, the E1B region lacking nucleotides that encode the viral oncoprotein, p55, and further includes other DNA sequences that are responsible for, or that enhance viral infection of host cells, or the production of progeny virus from host cells.

3. A method for treating cancer in an animal as described in claim 2 wherein said liposomal adenoviral DNA complex comprises cationic liposomes.

4. A method for treating cancer in an animal as described in claim 3 wherein said liposomal adenoviral DNA complex comprises a mixture of DC-Chol and DOPE.

5. A composition comprising a liposomal viral DNA complex for treating cancer in an animal in need of said treatment, said cancer comprising a cell population of non-neoplastic and neoplastic cells, said viral DNA being substantially purified adenoviral DNA not in an expression vector and incapable of encoding a functional viral oncoprotein that binds to a functional p53 tumor suppressor protein, and said viral DNA having the further properties of replicating and forming infectious virus in neoplastic cells lacking said tumor suppressor thereby killing said neoplastic cells and substantially incapable of replicating and forming infectious virus in non-neoplastic cells that have said tumor suppressor protein.

6. A composition comprising substantially purified adenoviral DNA in association with liposomal material as described in claim 5 wherein said adenoviral DNA includes the E1A and E1B regions of the viral genome, the E1B region lacking nucleotides that encode the viral oncoprotein p55.

7. Composition comprising adenoviral DNA as described in claim 6 wherein said liposomal adenoviral DNA complex comprises cationic liposomes.

8. A composition comprising a liposomal adenoviral DNA complex as described in claim 7 wherein said liposome comprises a mixture of DC-Chol and DOPE.

9. A method for producing adenovirus that is substantially selective for replicating in and lysing neoplastic cells that substantially lack the p53 tumor suppressor protein but not normal cells having functional p53 tumor suppressor protein, comprising the steps of;

administering to said neoplastic cells with an effective amount of a liposomal adenoviral DNA complex, said adenoviral DNA being substantially purified and not in an expression vector and that is incapable of encoding a functional viral oncoprotein that binds to said functional p53 tumor suppressor and said adenoviral DNA having the further properties of replicating and forming infectious virus in said neoplastic cells thereby killing said neoplastic cells; waiting a period of time for said adenoviral DNA to kill said neoplastic cells; and isolating said adenovirus from said killed neoplastic cells.

10. A method for producing adenovirus as described in claim 9 wherein said viral oncoprotein is p55.

* * * * *